United States Patent [19]

Cayrol

[11] Patent Number: 4,666,714
[45] Date of Patent: May 19, 1987

[54] NEMATOPHAGOUS AGENT AND A PROCESS FOR CONTROLLING THE GROWTH OF NEMATODA OF THE MELODOGYNIC SPECIES

[75] Inventor: Jean-Claude Cayrol, Biot, France

[73] Assignee: Institut National de la Richerche Agronomique INRA, Antibes, France

[21] Appl. No.: 479,120

[22] Filed: Apr. 1, 1983

Related U.S. Application Data

[63] Continuation of Ser. No. 48,275, Jun. 13, 1979, abandoned.

[30] Foreign Application Priority Data

Jun. 13, 1978 [FR] France .............................. 78 117624

[51] Int. Cl.[4] ...................... A01N 63/04; A01N 25/04
[52] U.S. Cl. ........................................ 424/93; 47/57.6; 71/3; 71/6; 435/243
[58] Field of Search .......................... 424/93; 435/243; 47/57.6; 71/3, 6

[56] References Cited

U.S. PATENT DOCUMENTS

| | | | |
|---|---|---|---|
| 3,013,946 | 12/1961 | Lumb et al. | 424/93 |
| 3,642,982 | 2/1972 | Morimoto et al. | 424/93 |
| 4,061,488 | 12/1977 | Mann | 71/77 |

FOREIGN PATENT DOCUMENTS

| | | | |
|---|---|---|---|
| 1151570 | 8/1983 | Canada . | |
| 2317881 | 11/1977 | France | 424/93 |
| 2402412 | 6/1979 | France | 424/93 |
| 2394606 | 12/1979 | France | 424/93 |
| 800736 | 9/1958 | United Kingdom | 424/93 |
| 972871 | 10/1964 | United Kingdom | 424/93 |
| 246958 | 11/1969 | U.S.S.R. | 424/93 |

OTHER PUBLICATIONS

Cayrol; Revue Zoologie 73:77–89 (1977).
Mordbring-Hertz; Ecol. Bull. (Stockholm) 25:483–484 (1977).
La Défense des Végétaux No. 20, Janvier-Féurier 1981, pp. 85–88.
La Défense des Végétaux No. 210, Juillet-Août 1981, pp. 279–282.
Cayrol et al., Revue de Zoologie 71:118–138 (1972).
Cayrol et al., P.H.M.-Revue Horticole 184: Feb. 23–30, 1978.
Cayrol et al., Mushroom Science X (Part II): 407–413 (1978).
Cayrol et al., P.H.M.-Revue Horticole 203:33–38 (Jan. 1980).
Cayrol ACTBS DU 97th Congres National des Societes Savantes (Nantes 1972), Sect. de Sciences Tome III.
Cayrol et al., Revue de Zoologie Agricole et de Patholosie Vegetalis 174:139–146 (1975).
Cayrol et al., P.H.M.-Revue Horticole 193: Jan. 15–23, 1979).
Cayrol et al., P.H.M.-Revue Horticole 164: Feb. 21–23, 1976.

Primary Examiner—Ronald W. Griffin
Attorney, Agent, or Firm—Weiser & Stapler

[57] ABSTRACT

A new nematophagous agent comprising the *Anthrobotrys irregularis* number 1 141 b strain and its use for controlling the growth of Nematoda of the meloidogyne species.

The agent is particularly useful for controlling Nematoda of the meloidgyne species in vegetables flowers and nursery plants.

20 Claims 8 Drawing Figures

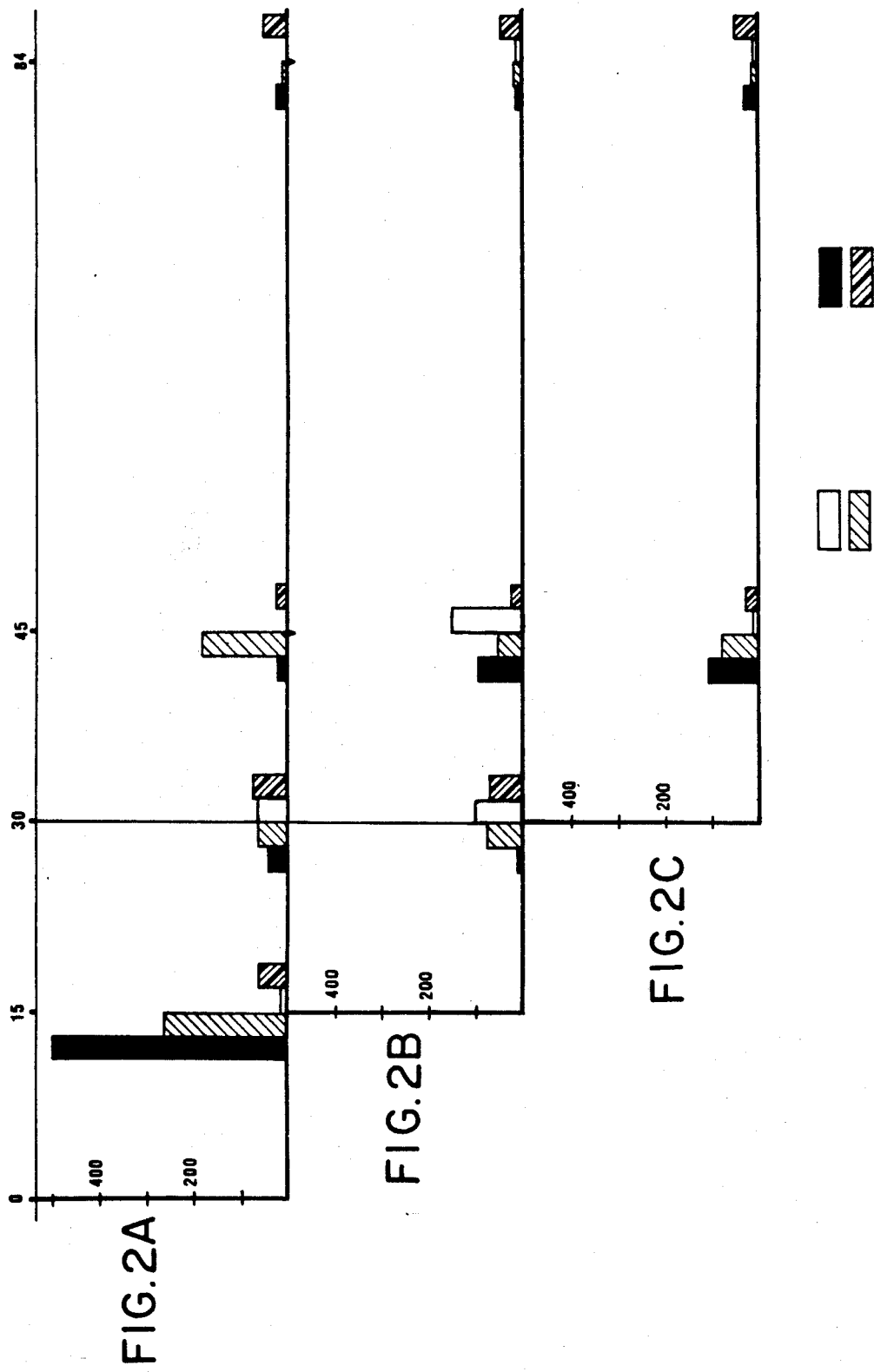

NEMATOPHAGOUS AGENT AND A PROCESS FOR CONTROLLING THE GROWTH OF NEMATODA OF THE MELODOGYNIC SPECIES

This is a continuation of application Ser. No. 048,275, filed June 13, 1979, now abandoned.

FIELD OF THE INVENTION

The present invention relates to a new nematophagous agent intended to fight against the nematoda of the meloidogynic species and also to a process for controlling the growth of these nematoda in vegetable and floral crops and in plants in nurserys.

PRIOR ART

The nematoda of the meloidogynic species, which are the nematoda of "knot-root", constitute one of the main enemies of crops, particularly of vegetable and floral crops, and especially in the warmer regions and in green-house crops. These namatoda, which are extremely polyphagous, attack virtually all crops and are therefore responsible for catastrophically low yields which often reach only 50 to 70%.

At present the only feasible process for fighting these nematoda involves repeated preventive disinfection of the ground before crop planting, using nematicidal products which are always expensive and dangerous.

An object of the present invention therefore is to provide a new nematophagous agent which allows the rapid multiplication of these nematoda parasites to be limited in a permanent and less expensive manner.

SUMMARY OF THE INVENTION

FIG. 1 is a schematic drawing of Arthrobotrys,
FIG. 1A illustrating the conidia,
FIG. 1B the trap,
FIG. 1C chlamydospores and
FIG. 1D conidiphores.
FIG. 2A, 2B and 2C illustrate the development of the moloidogyne cultures as a function of the dosages of Arthorobotrys Irregularis.

According to the present invention, the new nematophagous agent which is intended to fight the nematoda of the meloidogynic species is formed by a predatory fungus of the Hyphomycetes class, hereinafter called Arthrobotrys irregularis number 1 141 b. The strain of Arthrobotrys irregularis number 1 141 b which has been extracted from the earth, is similar to Arthrobotrys tortor which has recently been described by Nelly Jarowaja in Poland (1968-Arthrobotrys tortor sp. nov. New predacious nematoda killing fungi. Acta Mycologia, Vol. IV-2: 241–247).

Arthrobotrys irregularis number 1 141 b is a mycelium composed of septate Hyphae which are from 3.4 to 5.1 $\mu$m wide and which produce 3-dimensional loops approximately $32\mu$ in diameter. It exhibits hyaline conidiphores which are erect and septate (never branched), and which are from 6.8 to $8.4\mu$ wide at their base and $3.4\mu$ wide at their apex. It should be noted that, in contrast, the so-called Arthrobotrys tortor species described by Jarowaja, exhibits branching of the conidiphores end with an irregular swelling which is spikey and which has small thorn-shaped stigmata. The conidia are arranged in irregular groups at the end of the conidiphores. It will also be noted that intercalated conidia have never been observed along the conidiphore in the strain of Arthrobotrys irregularis number 1 141 b while Jarowaja, points out this characteristic in the description of his species.

The conidia are hyaline, egg-shaped and slightly rounded at their base. They are divided transversely in to two irregular cells, the lower cell ending with a downward point while the upper cell is round and swollen, the partition being almost in the centre of the conidium. The average size of the conidia is $27.7\mu$ in length by $11\mu$ in width.

The chlamydosphores are intercalated and globular, and are either isolated or are in short chains. Each chlamydosphore is approximately $25\mu$ in diameter.

The strain of Arthrobotrys irregularis number 1 141 b also has some similarities with the coniod Arthrobotrys described by drechsler Ch. (1937-some Hyphomycetes that prey on free living terricolous nematodes, Mycologia 29; 447 to 556), but it differs there from since it does not have intercalated conidia, but it is closer to Arthrobotrys tortor in all its characteristics and particularly in its conidia which are rounder and more thick set than those of Coniod Arthrobotrys, which are much more slender.

The attached FIG. 1 illustrates the conidia (A), trap (B), Chlamydosphores (C) and conidiphores (D) of Arthrobotrys irregularis 1 141 b.

The strain of Arthrobotrys irregularis number 1 141 b has formed the subject of the document filed at the Mycotheque of the Institute Pasteur on June 2nd, 1978 where it was recorded under number 1166–78.

The present invention also provides a process for controlling the growth of Nematoda of the meloidogynic species in the market gardening and flower crops as well as in plants in nurserys. The process is characterised by the fact that a suitable quantity of the nematophagous agent formed by the predatory fungus Arthrobotrys irregularis number 1 141 b, described above, is incorporated into the earth to be treated.

According to another characteristic of the process of the present invention, the nematophagous agent of the present invention is preferably positioned in the earth to be treated approximately 30 days before planting.

According to another characteristic of the present invention which is applicable to plants which can be delivered in balls of earth, small flower pots or containers, the nematophagous agent is incorporated directly into the centre of the ball, the small flower pot or the container.

According to another characteristic of the present invention the earth may be colonised by the nematophagous agent of the present invention prior to, or during, the planting of plants which do not themselves suffer from attack by meloidogynes because they only remain in position for a short time and/or they perform their cycle in winter when the meloidogynes are not active. Such a variation in the process of the invention allows the earh to be prepared for subsequent planting because of the remnant action of the nematophagous agent.

Other characteristics and advantages of the present invention will appear when reading the detailed description given below of several particular modes of operation and embodiments.

DETAILED DESCRIPTION

Figure 1A:
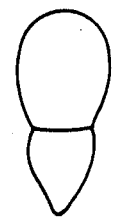
Figure 1B:
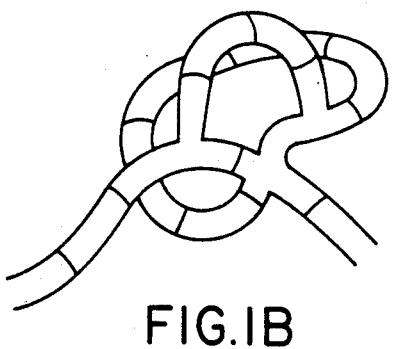
Figure 1C:
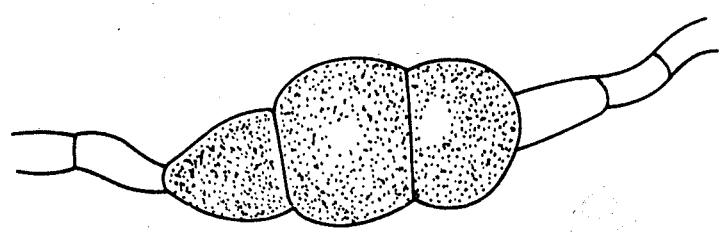
Figure 1D:
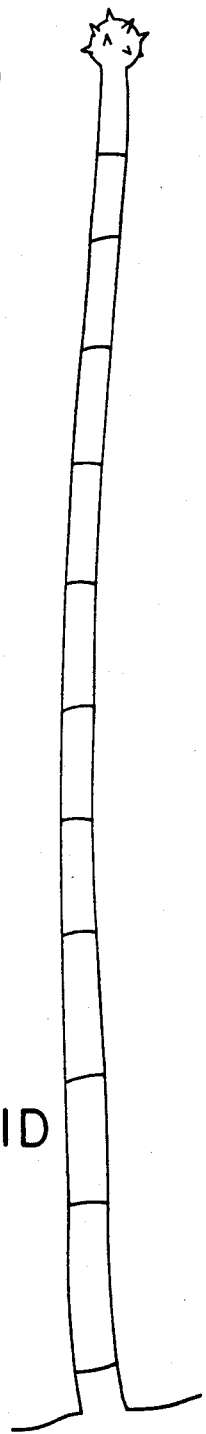

The strain of Arthrobotrys irregularis number 1 141 b has been selected from a large number of strains of predatory fungi which have been isolated in various types of French Earths. The aggresiveness of these various strains toward to meloidogynes was firstly tested by in vitro test carried out in mini culture. These in vitro tests involved spreading a film of water which has been treated with 0.5% gellose asceptically over a plate of glass. This film is then sown with the predatory fungus. Once the fungus has covered the entire surface, approximately 48 hours later, 10 L2 disinfected larvae of meloidogynes were deposited asceptically on the medium. Sterilization is achieved by immersion for about 1 minute in 1 per 1000 mercurothiolic acid and for 1 minute in 1 per 1000 streptomycine sulphate, followed by rinsing in sterile water. The size of the trapping is then noted regularly every 2 days over 10 days by observing each blade through a binocular lens in a sterile specimen. From the 31 species of predatory fungi tested, the *Arthrobotrys irregularis* number 1 141 b strain exhibited by far the greatest predatory activity towards these Nematoda as it distroyed about 90% of the yound meloidgynine lavae. It was then checked that the *Arthrobotrys irregularis* number 141 b strain actually captures and very quickly destroys all the newly hatched infesting yound larvae before they have had time to penetrate into the radicals of the host plant.

It has, moreover, been observed that *Arthrobotrys irregularis* number 1 141 b developed very rapidly. Owing to its very rapid mycelium growth, this strain can be used quite satisfactorily in practice as a nematophagous agent in vegetable and floral crop as well as in nursery plantations.

It has been observed during tests to examine the ability of the new strain to be implanted in various cultivated soils, that fungus establishes itself better in soils of neutral and alkaline conditions than in acidic soils. These results are therefore very interesting since vegetable and floral crops demand a pH of approximately 7, which therefore allows easy colonisation of the soil.

It has also been noted that the predatory fungus invades in a strong dosage, but this does not prevent it from colonising the substrates in an appreciable manner even in a dosage of 10% of the volume of earth.

The predatory activity of the *Arthrobotrys irregularis* 1 141 b strain has also been confirmed by a number of tests of practical application, whose the results of some of which are given below for information.

I. Green House Experiments on Crops of Tomatoes in Pots 40 pots which were filled with soils which had been sterilized by steam and divided into four batches of 10 were prepared for this experiment. The four batches are divided in the manner shown below.

TABLE 1

| | | |
|---|---|---|
| Without Predatory Fungus | Batch 1: | Each pot receives one tomato plant |
| | Batch 2: | Each pot receives one tomato plant and is infested with 1500 meloidogyne eggs deposited |

TABLE 1-continued

| | | |
|---|---|---|
| | | in the vicinity of the radicles |
| With Predatory Fungus | Batch 3: | Each pot receives one tomato plant |
| | Batch 4: | Each pot receives one tomato plant and is infested with 1500 meloidogyne eggs deposited in the vicinity of the radicles |

In batches 3 and 4, half of an *Arthrobotrys inoculum* prepared in Erlen-Meyer flasks on a medium based on bran, perlite and wheat cooked in the conventional manner, and used by vegetable pathologists, is incorporated in the soil.

The test is followed, on the one hand by noting the strength of the tomato plants which is expressed as a grade of from 0 to 5 (0=dead plant, 5=perfect, very vigorous plant) and, on the other hand, by periodically analysing the soil to follow the development of the cultures of Nematoda.

Results Concerning the Notation of the Plants

The results obtained are given in Table II. for each observation, they indicate the average strength of 10 plants in each batch.

TABLE II

| | CASES TESTED | | | | |
|---|---|---|---|---|---|
| Observations | tomatoes alone (healthy samples) | tomatoes + Meloidgyne | tomatoes + Predatory fungus | tomatoes + meloidogyne + Predatory fungus | Important Remark |
| Day 0 | 1.30 | 0.60 | 0.70 | 0.90 | On day 20, the tomatoe planted in the inoculum of Predatory Fungus were pricked in to normal soil. The notations can therefore only be compared truely from day 30. |
| Day 10 | 1.80 | 1.30 | 0.90 | 0.80 | |
| Day 20 | 1.20 | 1.70 | 1.08 | 1.07 | |
| Day 30 | 2.30 | 1.20 | 1.80 | 1.90 | |
| Day 40 | 2.20 | 2.00 | 2.60 | 2.50 | |
| Day 50 | 2.60 | 2.10 | 2.50 | 2.30 | |

It is observed that up until day 30 the plants are still weaker in the cases where they have been planted in the inoculum of predatory fungus. This is easily explained since the inoculum based on bran, perlite and baked wheat constitutes a magma which is rich in sugar and which is therefore very beneficial to the development of bacteria and various small flies which considerably obstruct the growth of the roots.

In order to avoid this phenomenon, the plants were pricked into larger pots containing sterile humus from the 30th day. As a result, the inoculum of predatory fungus remained present in the pricked ball, but the new roots formed could develop normally in the medium.

From this date, the results of the form batches can be compared, and it is observed in all cases that the presence of the predatory fungus allows the growth of tomatoes which are comparable to the healthy samples, and which are more vigorous than those infested by the Meloidogyne, to be obtained.

Results Concerning the Development of the Cultures of Meloidgyne

Table III below summarizes the development of the cultures of meloidogyne throughout the duration of the experiment.

| Observations | CASES TESTED | | | |
|---|---|---|---|---|
| | tomatoes alone (healthy samples) | tomatoes + Meloidogyne | tomatoes + predatory fungus | tomatoes + Meloidogyne + predatory fungus |
| Day 10 | 0 | 0 | 0 | 0 |
| Day 20 | 0 | 45 | 0 | 70 |
| Day 30 | 0 | 20 | 0 | 35 |
| Day 40 | 0 | 35 | 0 | 0 |
| Day 75 | 0 | 29 | 0 | 0 |

It appears that Meloidogyne is never found in the non-infested healthy sample without a predatory fungus, nor in the batch inoculated only with Hyphomycete, and this proves that the humus used was sterilized correctly and that no accidental recontamination took place during the test.

With regard to the two other cases, it is observed that from the 40th day all the meloidogyne have disappeared from the batch treated with the predatory fungus whereas they are present until the end of the experiment (75 days) in the contaminated batch.

It therefore very clearly appears that about one month is needed for the *Arthrobotrys irregularis* number 1 141 b to establish itself in the soil and for it to afford effective protection for the plants.

These experiments therefore show that the method of preparing the inoculum of the predatory fungus is important because, if the predatory fungus is introduced into an unsuitable inoculum, it is liable to cause disturbances at the level of the substrate which interfere with the root development of the plants. The inoculum has consequently been prepared in the form of granules in the following manner. Seeds of cereals, for example rye, which have been cooked in steam in an autoclave are used as starting materials, and these seeds are then sown with the predatory fungus. In order to allow the seeds to be sown in this way, nutrients are added in the conventional manner to the cereal seeds which have been sterilized in steam and which contain approximately 45 to 50% of water, and the predatory fungus therefore develops throughout the mass of all the cereal seeds. For example, calcium salts such as calcium carbonate are added to the grains of cereals. In practice, this method of preparing the predatory fungus inoculum has given quite satisfactory results.

The test just described also shows that the predatory fungus needs approximately one month to colonise the medium properly and to exhibit real activity towards the meloidogyne. This is why the nematophagous agent is preferably be positioned in the soil to be treated approximately 30 days prior to the introduction of the crop to be protected.

With cultivation in open fields, the soil can be colonised by scattering and burying grains of cereals which have been cooked in steam and sown with the predatory fungus. The effective dose when treating granules on the soil and then burying them with for example a claw cultivator or a light plough is generally between 50 and 300 g per m² of soil to be treated, depending upon the amount of meloidogyne expected to be encountered.

II. Green House Experiments on Tomato Crops

Method 102 plastic pots having a diameter of 15 cm were filled with 1600 g of soil (i.e. about 2 l) originating from a plot of land which had been badly infested by meloidogyne. These pots were divided up into 12 pots which were kept as test samples and 90 pots which were treated with *Arthrobotrys irregularis* number 1 141 b under varying conditions (different dosages and nubers of days).

During the experiment described above, it appeared to be necessary to allow one month for the fungus to colonise the soil well and thus to reach its maximum effectiveness. In this second test, the nematicidal capacity of *Arthrobotrys irregularis* number 1 141 b was compared, depending on whether it was introduced into the substrate one month before plantation, 15 days before plantation or on the actual day of planatation.

Planting involves placing a stalk of healthy tomatoes in each pot.

The overall experimental procedure is compiled in Table IV below.

TABLE IV

| Doses of inoculum of Arthrobotrys 1 141 b per pot | Dates of inoculation of the predatory fungus | | |
|---|---|---|---|
| | 30 days before planting A | 15 days before planting B | Day of Planting C |
| 1.4 gramme | 10 pots | 10 pots | 10 pots |
| 2.8 grammes | 10 pots | 10 pots | 10 pots |
| 5.6 grammes | 10 pots | 10 pots | 10 pots |
| non-inoculated control sample | | 12 pots | |

The test was carried out for 84 days with regular analysis of the average culture of meloidogyne larvae found in the soil in each case, compared with the control samples. The root system of the plants was also analysed at the end of the test.

Results

All the results obtained in this experiment are illustrated schematically in a composite histogram as FIG. 2 of the attached drawings. FIG. 2 actually shows the development of the meloidogyne cultures as a function of the dosages of *Arthrobotrys irregularis* 1 141 b inoculum and the dates of inoculation. The zone (A) corresponds to the inoculation of the fungus 30 days before planting; zone (B) 15 days before planting and zone (C) on the actual day of planting.

Examination of this histogram shows that the meloidogyne cultures are always large with the weak dose (1.4 g per pot, that is to say 70 g/m², except that at the end of the experiment when this dosage manages to reduce the number of Nematoda in comparison with the control sample).

With the average dosage (2.8 g per pot, that is to say 140 g/m²), the results are very similar, but better than with the weak dosage.

Finally, the meloidogyne only disappear completely if the fungus is introduced one month before planting (case A) with the strong dosage (5.6 g per pot, that is to say 280 g/m²).

The roots were analysed at the end of the experiment and the results, which are shown in Table V, confirm the data obtained by soil analysis.

TABLE V

The results indicated represent the average number of Nematoda per gramme of roots

| Periods of inoculation with Arthrobotrys | Stages of Development of meolidgyne | TREATMENTS | | | |
|---|---|---|---|---|---|
| | | Weak dose (70 g/m$^2$) | Average dose (140 g/m$^2$) | Strong dose (280 g/m$^2$) | Untreated control sample |
| A (30 days before planting) | Females | 1.1 | 1.6 | 0 | 6.4 |
| | Larvae | 1.4 | 1.2 | 0 | 4.0 |
| | Eggs | 3.0 | 4.7 | 0 | 2.0 |
| B (15 days before planting) | Females | 0.1 | 0.8 | 0.4 | 1.3 |
| | Larvae | 0 | 0.5 | 0.3 | 0.8 |
| | Eggs | 0 | 0.6 | 0 | 0.8 |
| C (day of planting) | Females | 1.9 | 2.0 | 1.6 | 1.0 |
| | Larvae | 0 | 4.7 | 2.3 | 2.0 |
| | Eggs | 9.3 | 2.0 | 2.0 | 0 |

It is in fact seen that the meloidogynes are only destroyed completely with strong doses (280 g/m$^2$) inoculated one month before planting.

In all the treatment A and B (sowing 30 days and 15 days before planting) the cultures are always very much smaller than the control samples but this might not be sufficient to provide perfect protection for the plants, at least in the present case where the initial nematological infestation was obviously extremely high.

With regard to case C (sowing on day of planting), the *Arthrobotrys irregularis* number 1 141 b turned out to be completely inactive, and this confirms the previous experiment in which it needed about one month to colonise the soil sufficiently and to be really effective.

It should however be noted that it will not be necessary to use such a high dose in the majority of practical cases since it should not be forgotten that the test was carried out with a very highly contaminated soil, and under conditions of temperature and humidity which are extremely favourable to the proliferation of the parasite.

These are conditions which are never encountered in practice.

Furthermore, the inoculated soils are colonised definitively by the predatory fungus and this provides protection for a long period, contrary to the chemical nematacidal agents whose action is transitory.

Various experiments intended to demonstrate the remnant action of the treatment have in fact shown that it is possible to benefit from an early crop of potatoes which have been planted around the month of February and harvested about the month of June to colonise the soil with the aid of *Arthrobotrys irregularis* 1 141 b in order to protect, for example, a crop of tomatoes planted in the same plot later on. In the particular case of early potatoes which are positioned in February and with simultaneous treatment of the soil, it is possible to obtain protection lasting until September of the same year. Thus, in accordance with a variation of the process according to the present invention, the soil can be treated during a short spring crop in order to protect the long summer crop which will follow thereafter.

The process according to the present invention can obviously be applied to any vegetable or floral crops or nursery plants, all these crops being sensitive to meloidogyne. It should, however, be noted that some of these plants do not suffer from meloidogynes either because they only remain in position for a short time, e.g. radishes, various beans, peas and the like or because they have their growing cycle in winter at a time when the meloidogynes are not active.

According to an interesting variation of the process according to the present invention, it is therefore possible to colonise the soil with the nematophagous agent just before planting plants which do not themselves suffer from attack by meloidogynes. The remnant action of the nematophagous agent therefore allows the soil to be prepared for plants which will be planted later on and which are sensitive to these Nematoda.

The present invention also provides another very interesting variation of the process for controlling the growth of the Nematoda of the meloidogyne type in vegetable and flora crops as well as in nursery plants. At present, market gardeners rarely grow their own plants from seed and the like and buy "ready to plant" plants from establishments which specialise in their production them. Plants of this type can therefore be delivered in balls, in small green houses or even in containers, for example in the case of fruit trees.

According to a variation of the process of the present invention, sowing with the predatory fungus is carried out from the beginning in pressed balls which are used for producing vegetable plants. By following this procedure, it has been found that, during the 20 to 30 days when the newly pricked plants in the balls remain in the heat and humidity of the green house, the predatory fungus has time to grow and invade the entire ball which then itself behaves as an inoculum when it is positioned during cultivation.

This variation of the process according to the invention which is applicable to plants which can be delivered in balls, small pots, containers or the like has turned out to have the following advantages.

The soil which is normally used for making up balls is a mixture which is rich in humus and which has a pH of 7. It is therefore particularly favourable toward the development of *Arthrobotrys irregularis* number 1 141 b. It has also been observed that the radicle system of the plant is literally surrounded in the mycelium packing which does not however disturb its growth at all. The radicle system is therefore protected from attack by Nematoda, even if the ball is planted in a particularly contaminated soil. It therefore appears that the young plant is well protected from the beginning of vegetation, and this is particularly advantageous since plants are generally most susceptible to attacks by Nematoda when they are young whereas they hardly suffer from nematological attacks at all when they are old and have already developed an abundant root system.

The various experiments carried out have demonstrated that the ball constitutes a significant inoculum from which the fungus very easily reaches the surrounding soil. These balls, small pots, containers or the like can be prepared without the slightest technical problem in the use or production of plants. It is in fact, sufficient to introduce the granules into the mixture, for example with the aid of a hopper. Furthermore, the plants prepared in this way are planted in a quite conventional manner. In practice, the cereal grains which have been sown are incorporated in a satisfactory manner in a proportion of about 3 g of granulates for about 100 g of earth.

Whether the cereal grains sown are used in a proportion of 2, 4 or 8 g per 150 g ball of earth, the ball is in all cases invaded completely by the white packing of the fungus at the moment of planting and the protection from nematological agression turns out to be satisfactory in practice.

Of course, the present invention is not limited to the particular embodiments and modes of operation described and it is possible to imagine a certain number of variations in the details without departing from the scope of the present invention. Thus, it should be emphasised that the nematophagous agent and the process according to the invention can be applied quite satisfactorily to any vegetable crops, any floral crops and any nursery plantations. Examples of vegetables which are delivered in a pressed ball include tomatoes, aubergines, sweet peppers, courgettes, melons, various lettuces (e.g., cos lettuces, endives and curly lettuces). Examples of vegetable crops which are not delivered in balls include artichokes, carrots, potatoes (summer crop), beetroots and celery. Examples of cultivated flowers likely to be protected according to the present invention include, cut flowers such as carnations, rose bushes, gerberas and chrysanthemums., pot plants with decorative foilage such as all the green house plants, philodendrons, figs, pothos, sansevierias, cacti, merentas and phenix,) as well as potted flowers such as cinerairias, cyclamens, primroses and saint paulias. Examples of nursery plants which are usually delivered in containers include all the ornamental and fruiting shrubs.

The process according to the present invention will either be carried out by scattering and burying the inoculum or placing the inoculum directly into the ball or the like depending upon whether the crop is in open fields or is in the form of plants which can be delivered in balls, small pots, containers or the like.

What is claimed is:

1. A nematocidal composition effective to control the growth of the meloidogyne species of nematode thirty days after the soil is inoculated with the composition which composition comprises an agriculturally acceptable carrier and, in an amount effective to control said meloidogyne after thirty days, the man-isolated, man-selected from other man-isolated Hypohmycetes class of predatory soil fungi, *Arthrobotrys irregularis* strain No. 1.141b.

2. The composition of claim 1 wherein the selection is made from man-isolated Arthrobotrys predatory soil fungi.

3. The composition of claim 2 wherein the selection is that of selecting the fungi which exhibits the greatest trapping of meloidogyne larvae.

4. The composition of claim 3 wherein the selected strain destroys at least about 90% of young meloidogynine larvae.

5. The composition of claim 4 wherein the selected strain destroys all the newly hatched infesting young larvae.

6. The composition of claim 1 for control of the growth of the meloidogyne species of nematode wherein the man-isolated predatory fungi is selected from Arthrobotrys genus of the Hypomycetes class.

7. The composition of claim 6 wherein the control is the killing of the meloidogyne.

8. The composition of claim 7 wherein the killing of the meloidogyne is complete.

9. The composition of claim 6 wherein the carrier is cereal seed.

10. The composition of claim 6 which further comprises a nutrient for the *Arthrobotrys irregularis* strain No. 1.141 b.

11. The composition of claim 2 wherein the strain is that deposited at Institut Pasteur Mycotheque, Paris, France under accession No. 1166-78.

12. The composition of claim 7 wherein the *Arthrobotrys irregularis* strain No. 1.141b is developed throughout the mass of the composition.

13. The composition of claim 10 wherein the nutrient is a calcium salt.

14. The composition of claim 13 wherein the calcium salt is calcium carbonate.

15. The composition of claim 9 wherein the seed is rye seed.

16. The composition of claim 9 wherein the seed is sterilized.

17. The composition of claim 9 wherein the seed contains 45% to 50% water.

18. A nematocidal composition effective to control the growth of the meloidogyne species of nematode thirty days after the soil is inoculated with the composition which composition comprises man-isolated, man-selected Hypohmycetes class of Arthrobotrys predatory fungi, *Arthrobotrys irregularis* strain No. 1.141b deposited at the Institut Pastuer Mycotheque, Paris, France under accession number 1166-78, a calium salt nutrient for the strain No. 1.141b and cereal seed,
wherein the selection of strain consists of selecting the strain which destroys at least 90% of the young meloidogyne larvae and all of the newly hatched infesting young larvae, and
the *Arthrobotrys irregularis* shown No. 1.141b is developed throughout the mass of the composition.

19. A man-made culture of *Arthrobotrys irregularis* strain No. 1.141b which culture includes a nutrient medium and the culture of the strain, which strain is nematocidal and effective to kill at least 90% of the larvae of the species of "knot-root" causing nematode meloidoygnes thirty days after the soil is inoculated with that culture strain No. 1.141b, wherein the strain is man-cultured after having been man-isolated and man-selected from other man-isolated Hyphomeycetes class of Arthrobotrys predatory fungi, which other strains are not effective to so kill the species of "knot-root" causing nematode meloidoygnes thirty days after innoculation of the soil.

20. The composition of claim 19 wherein the strain is that deposited at Institut Pasteur Mycotheque, Paris, France under accession number 1166-78.

* * * * *

UNITED STATES PATENT AND TRADEMARK OFFICE
CERTIFICATE OF CORRECTION

PATENT NO. : 4,666,714
DATED : May 19, 1987
INVENTOR(S) : Jean-Claude Cayrol

It is certified that error appears in the above-identified patent and that said Letters Patent is hereby corrected as shown below:

[73] Delete "Richerche" and replace by --Recherche--.

[30] Delete "78 117624" and replace by --78 17624--.

Signed and Sealed this

Twenty-ninth Day of August, 1989

*Attest:*

DONALD J. QUIGG

*Attesting Officer*  *Commissioner of Patents and Trademarks*